Figure 1:
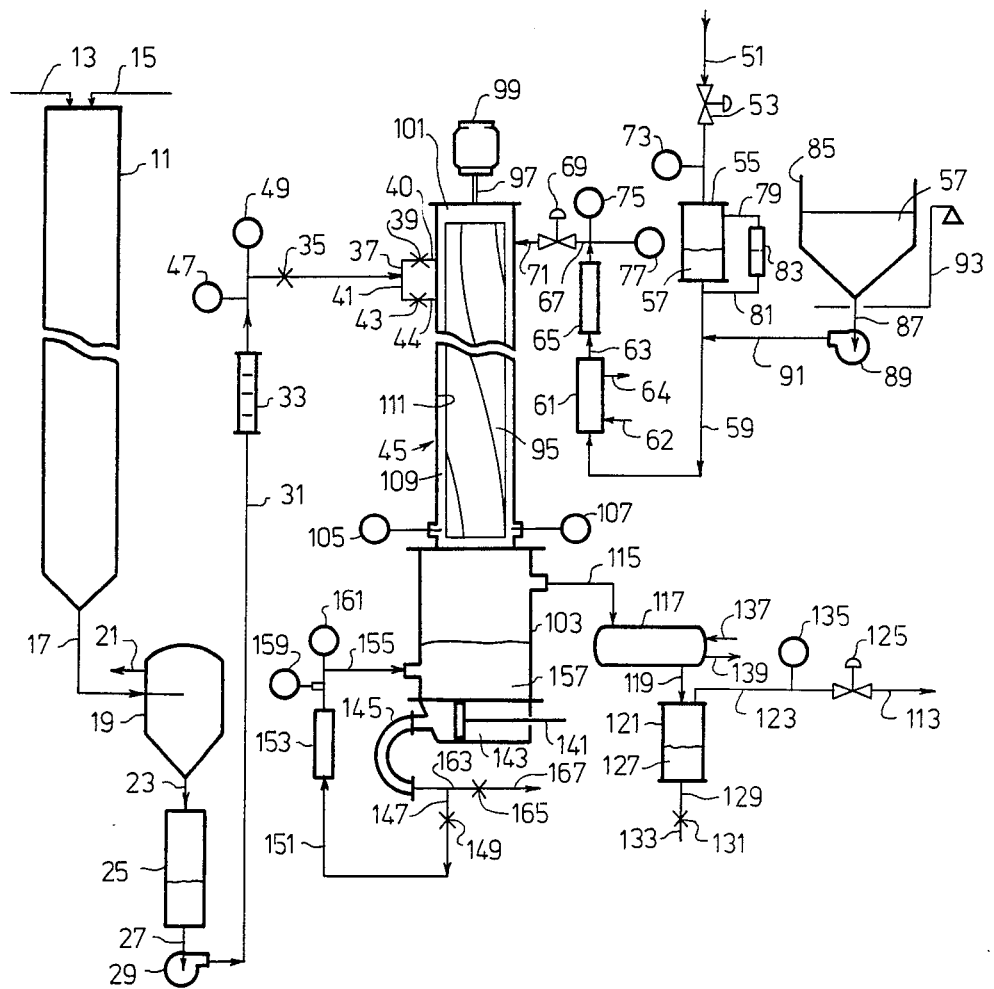

United States Patent [19]

Silvis

[11] Patent Number: 4,544,493
[45] Date of Patent: Oct. 1, 1985

[54] NEUTRALIZATION OF ORGANIC SULFURIC OR SULFONIC DETERGENT ACID TO PRODUCE HIGH SOLIDS CONCENTRATION DETERGENT SALT

[75] Inventor: Salvatore J. Silvis, Staten Island, N.Y.

[73] Assignee: Colgate-Palmolive Company, New York, N.Y.

[21] Appl. No.: 534,570

[22] Filed: Sep. 22, 1983

[51] Int. Cl.$^4$ .......................................... C07C 141/04
[52] U.S. Cl. .................... 252/89.1; 252/549; 252/184; 260/459 R; 422/137; 422/229
[58] Field of Search ...................... 252/89.1, 182, 184, 252/549; 260/459 R; 422/137, 225, 229

[56] References Cited

U.S. PATENT DOCUMENTS

| | | | |
|---|---|---|---|
| 2,687,420 | 8/1954 | Brady | 260/400 |
| 2,939,770 | 6/1960 | Schwartzkopff et al. | 422/229 |
| 3,200,140 | 8/1965 | Sowerby | 422/189 |
| 3,473,896 | 10/1969 | Halder et al. | 422/229 |
| 4,322,367 | 3/1982 | Silvis | 260/459 R |

Primary Examiner—John Kight
Assistant Examiner—Nathan M. Nutter
Attorney, Agent, or Firm—Richard N. Miller; Murray M. Grill; Herbert S. Sylvester

[57] ABSTRACT

A process for neutralizing an organic sulfuric or sulfonic detergent acid, e.g., lauryl sulfuric acid or mixture of such acids, in liquid state, with a liquid solution or slurry of neutralizing agent of a low moisture content is conducted in a wiped film neutralizing reactor wherein a film of the organic acid(s) and neutralizing agent(s) is formed on an internal wall of the reactor, which wall (with the film) is continuously wiped during the neutralization reaction by a wall scraper or a plurality of scrapers which also agitate the reactants, whereby there is produced a pumpable aqueous slurry, having a high concentration of the detergent salt solids which is above a gel region which prevents the concentration of such detergents made by other processes that produce lower detergent concentrations. During the reaction, which is usually preferably conducted under vacuum, the heat generated is removed, usually by evaporation of water, so as to maintain a desirable temperature for the neutralization.

Also within the invention are processes wherein the wiped film neutralizing reactor is employed in conjunction with a film reactor for sulfating or sulfonating organic material, such as lauryl alcohol, to the corresponding detergent acid and soon after production thereof neutralizing such acid in the wiped film neutralizing reactor as well as the apparatus for practicing these processes.

18 Claims, 2 Drawing Figures

NEUTRALIZATION OF ORGANIC SULFURIC OR SULFONIC DETERGENT ACID TO PRODUCE HIGH SOLIDS CONCENTRATION DETERGENT SALT

This invention relates to neutralizing of detergent acids to produce detergent salts, useful for incorporation as detergents in dentifrices, shampoos, cosmetics, detergents and cleansers for hard surfaces. More particularly, it relates to the manufacture of sodium salts of organic sulfuric and/or sulfonic detergent acids by reaction of such acid(s) with neutralizing agent(s) in a wiped film neutralizing reactor to produce a concentrated aqueous solution of the detergent salt, e.g., sodium lauryl sulfate, of excellent quality. In a broader aspect of the invention detergent acid and neutralizing agent of sufficiently low moisture content(s) are reacted to make a high active ingredient detergent salt product that is of sufficiently low moisture content as to be non-gelling. The invention also relates to processes for such neutralization wherein the detergent acid is produced in a film reactor and the neutralized detergent salt is dried in a wiped film evaporator and is converted to solid sheet, ribbon or chip form. Combination apparatuses for use in practicing the described processes are also within the invention.

Although some synthetic organic detergent acids may be useful in unneutralized form, such acids will normally be neutralized to water soluble detergent salt form so as to make them suitable for employment in aqueous systems, which are those used in normal laundering and cleaning operations, and are present in various cosmetics and personal care items, such as dentifrices. Various such detergent salts have been employed in dentifrices, shampoos, cosmetics, laundry detergents and cleansers for hard surfaces, and other products, and while such detergents may be based on neutralized organic phosphorus-, nitrogen- and carbon-based acidic compounds, usually they will be sulfuric reaction products, either sulfates or sulfonates. Such sulfuric reaction products may be made by sulfation or sulfonation of lipophilic compounds or moieties by sulf(on)ating agents, such as oleum, sulfur trioxide or sulfuric acid, to produce what may be termed "sulfuric reaction acids" which are then neutralized, as by an alkali metal hydroxide. However, use of sulfuric acid or oleum introduces a source of water into the sulf(on)ating reaction and therefore sulf(on)ating with sulfur trioxide is often highly preferred. When water is present hydrolysis of the detergent acid can occur, with undesirable decomposition thereof. Sulfur trioxide sulfonation also limits the sulfate byproduct content of the detergent salt in the neutralized product.

When a detergent acid, such as one which will be called a sulfuric reaction acid or a sulfuric reaction detergent acid (which will be a sulfuric acid and/or a sulfonic acid having a lipophilic moiety in desirable hydrophilic:lipophilic balance, when neutralized, so as to result in a useful detergent), is neutralized, the neutralizing agent utilized, such as sodium hydroxide, will desirably be in aqueous solution. However, the neutralization reaction, if improperly controlled, can cause hydrolysis or other deterioration of the detergent acid or salt, leading to the production of off-specification materials. In the past, such degradation has been limited or inhibited by practicing neutralization processes wherein the reactants were dissolved and/or dispersed in a "heel" of already neutralized detergent solution or suspension, which heel would be kept in constant movement or circulation to avoid localized overconcentrations, overheatings, and pH variations. While such dispersing of the reactants did tend to prevent overconcentrations thereof, helped to limit excessive heating and degradation of the reactants and the product and helped to maintain the desired fluidity of the system, the product concentration would normally be held below any gelation point for such system, e.g., below about 33% of sodium lauryl sulfate in water solutions (for which the gel region extends from about 35% to about 49% of the sulfate). However, often it is desirable to produce neutralized detergent at a higher concentration, such as one over 50 or 55%, but the concentration of a lower active ingredient content detergent solution to such higher concentration, as by evaporation of water, becomes impossible because of the presence of a gel region. Thus, such processes are not feasible for the manufacture of high solids content, essentially 100% active ingredient or essentially 100% solids detergent product. Also, excessive power can be consumed in pumping the mixture of heel and reactants and care must be taken, especially if concentrations of detergent near the lower end of the gel range are being made, that variations in concentrations of the detergent salt do not develop, which could cause gel production and resulting blockages of the circulation system.

If an attempt is made to operate above the gel region, at higher concentrations of the neutralizing alkali and employing conventional mixer-type neutralizing equipment, localized pH variations and overheatings can lead to deterioration of the product. Also, even when heels or circulating finished product streams are employed to dilute the reactants, if one attempts to employ higher concentrations of neutralizing agent and essentially pure sulfuric reaction detergent acid to operate in an area above the gel range concentration of neutralized salt, overconcentration problems can occur due to the mass additions of reactants, leading to off-specification detergent salt being made and sometimes leading to gelation of the product in the neutralizer. Of course, when quality controls show that the product is off-specification due to degradation during the reaction, the equipment has to be cleaned out and large quantities of material have to be scrapped or "worked off" in less valuable products, leading to significant financial losses. Therefore, it is important that in manufacturing a high solids content aqueous detergent product the neutralization reaction should produce a high quality detergent salt, without objectionable degradation thereof during manufacturing, and should not result in gelation, which could cause further degradation of the product due to overconcentrations of reactants and localized overheatings caused by the heat of neutralization, and could solidify the product in the apparatus, leading to expensive cleanouts and losses of materials.

In accordance with the present invention a process for neutralizing an organic sulfuric or sulfonic acid(s) or a mixture thereof, suitable for use as a detergent in neutralized salt form, comprises feeding a liquid solution or slurry of neutralizing agent(s) and organic sulfuric acid(s) and/or organic sulfonic acid(s) in liquid state to a walled reaction zone, forming a film of such neutralizing agent(s) and organic acid(s) on a wall of such zone, contacting said film with means for limiting film buildup in said zone, which means continuously wipe the wall of said zone and thereby limit the thickness of the film, reacting said neutralizing agent(s) and organic acid in the film in said zone to produce neutralized organic sulfate and/or sulfonate detergent salt(s), removing heat of reaction from the film, moving the film through the reaction zone and removing the detergent salt(s) product, formed in said film reaction, from said reaction zone in the form of a pumpable aqueous medium containing from 50 to 85% by weight of said detergent salt(s) solids. Preferably, the detergent acid is one containing a single sulfuric acid or sulfonic acid moiety and a higher lipophilic alkyl group of 8 to 20 carbon atoms, such as lauryl sulfuric acid, the neutralizing agent is an aqueous solution of sodium hydroxide, the neutralization reaction takes place at a temperature of at least 40° C. in a wiped film reactor of vertically oriented cylindrical construction (although other inclinations than vertical are also operative), heat of neutralization is removed by vacuum vaporization of water (with the degree of vacuum controlling the reaction temperature), the scraper vanes of such a reactor rotate about the axis of the reactor cylinder and the blade tips of said scrapers are within 0.2 to 3 mm. of the interior wall of the reactor, preferably within 0.5 to 1 mm. thereof, the tip speed of the scraper vanes of such a reactor is in the range of 5 to 25 meters per second, and the product resulting contains at least 60 or 65% of neutralized detergent active ingredient, e.g., sodium lauryl sulfate, no more than 25 or 28% of water, and is of a color no darker than 75 Klett. In a broader sense the invention is of reacting a detergent acid, e.g., lauryl sulfuric acid, with a neutralizing agent, e.g., aqueous sodium hydroxide, at a total moisture content low enough (less than 45%, including any moisture resulting from the neutralization) so that the neutralized product is outside the gel region. Preferably, the preferred wiped film neutralizing process is utilized in conjunction with a sulf(on)ating process and an evaporation process, such as one wherein a film reactor is employed to manufacture the detergent acid, which is neutralized in the wiped film reactor, after which the concentration of the neutralized detergent is increased by evaporation in a wiped film evaporator. Also within the invention is the described combination of the three apparatuses for effecting sulf(on)ation, neutralization and concentration or evaporation.

A search resulted in the finding of U.S. Pat. Nos. 2,687,420; 2,690,446; 3,200,140; 4,113,438; and 4,153,625, all of which are directed to processes and apparatuses for neutralizing organic sulfonic and sulfuric acids, for the production of surface active agents, by bath, heel or circulation processes. Also found were U.S. Pat. Nos. 2,063,065; 2,768,199; 3,438,742; 3,547,593; and 3,620,684, which relate to scraped or wiped film apparatuses and processes.

U.S. Pat. No. 2,687,420 describes the neutralization of a sulfonation reaction mixture with aqueous sodium hydroxide solution by feeding both reactants to a reaction vessel in such proportions as to maintain the pH of the vessel contents substantially neutral. U.S. Pat. No. 2,690,446 utilizes sub-atmospheric pressure to aid in cooling detergent acid, neutralizing agent and the neutralized product solution in a reaction vessel through which the previously neutralized detergent solution is circulated. At the same time streams of the detergent acid and neutralizing agent are introduced into the agitated circulating stream of neutralized material. Cooling of the reaction mix is effected by flash cooling, or by evaporation of moisture from the mix. U.S. Pat. No. 3,200,140 describes the production of lauryl sulfuric acid from lauryl alcohol and sulfur trioxide, followed by neutralization in aqueous alkali to produce an aqueous solution of sodium lauryl sulfate of good color, but only of 27% active ingredient concentration. U.S. Pat. No. 4,113,438 teaches the manufacture of linear dodecylbenzene sulfonate and alcohol ether sulfate detergents by feeding sulfur trioxide and organic starting materials before the venturi of a venturi-type reactor. In Example II neutralization of the alcohol ether sulfuric acid is mentioned briefly. U.S. Pat. No. 4,153,625 teaches the removal of the heat of neutralization during neutralization of detergent acid, by cooling the reaction mix with a heat exchanger. The inventive feature of this patent is in the use of an aqueous slurry of sodium sulfate to reduce the deposition of such sulfate on heat exchanger surfaces. The patent mentions the formation of a recirculating neutralized detergent stream to dilute the acid mix prior to neutralization and to help to control the temperature upon neutralization.

U.S. Pat. No. 2,063,065 is of interest because it shows the scraping of heat transfer walls of a chilling apparatus, useful for chilling ice cream, margarine or the like. U.S. Pat. No. 2,768,199 describes the use of a Votator (described in U.S. Pat. No. 2,063,065) for the reaction of sulfur trioxide and sulfonatable organic material. However, the product resulting was not neutralized in the wiped film apparatus. U.S. Pat. No. 3,438,742 describes an apparatus for sulfur trioxide sulfation of organic compounds. The apparatus includes a cylindrical drum with projecting pegs to cause turbulence in a vertical reactor. Cooling of the reaction mix is effected by a cooling jacket. Neutralization with dilute sodium hydroxide solution is mentioned in the patent but it is apparently not conducted in the described reactor. Among the more relevant of the patents found in the search is U.S. Pat. No. 3,547,593, which describes a film reactor for carrying out chemical reactions in a film of liquid. The reactor includes a plurality of internally grooved drums and annular discs on the ends of such drums. The drums contain internal vertical grooves with openings in the crests between them, through which crest openings reactants may be discharged onto an annular heat exchange surface of the reactor, either before or after mixing of such reactants. There is no disclosure in the patent of a neutralization reaction and there is no statement that the reactor is a wiped film reactor. In view of the different structures it is considered that the grooved drums are significantly different from wiping blades and have a different effect and mode of operation, compared to blades of the present invention. U.S. Pat. No. 3,620,684 relates to sulfonation processes and apparatuses, not neutralization reactions. Although the detergent acid is neutralized, neutralization is not taught to be effected in the described apparatus. The apparatus includes two externally cooled and substantially concentric circular reaction surfaces, a reaction space between them of relatively small thickness, and a rotor located between such surfaces.

Also found in the search were U.S. Pat. Nos. 2,693,479; 2,909,534; 2,909,634; 3,337,601; and 4,163,751, all of which are considered to be of lesser relevance to this invention than the patents previously discussed, or are considered to be only cumulative.

From the above description of the patents found in the search it appears that the use of the wiped film reactor described herein for neutralization of detergent acids is novel and unobvious. While it may be questioned whether any of the apparatus patents found in the search which describe detergent reactions are true wiped film reactors it is recognized that wiped film reactors per se have been marketed and such are not claimed in this application, except in conjunction with other apparatuses with which they are to be jointly employed. The broader aspect of the invention, employing low moisture content detergent acid and neutralizing agent to make a non-gelling detergent salt, such as sodium lauryl sulfate, also appears to be patentable.

Figure 2:
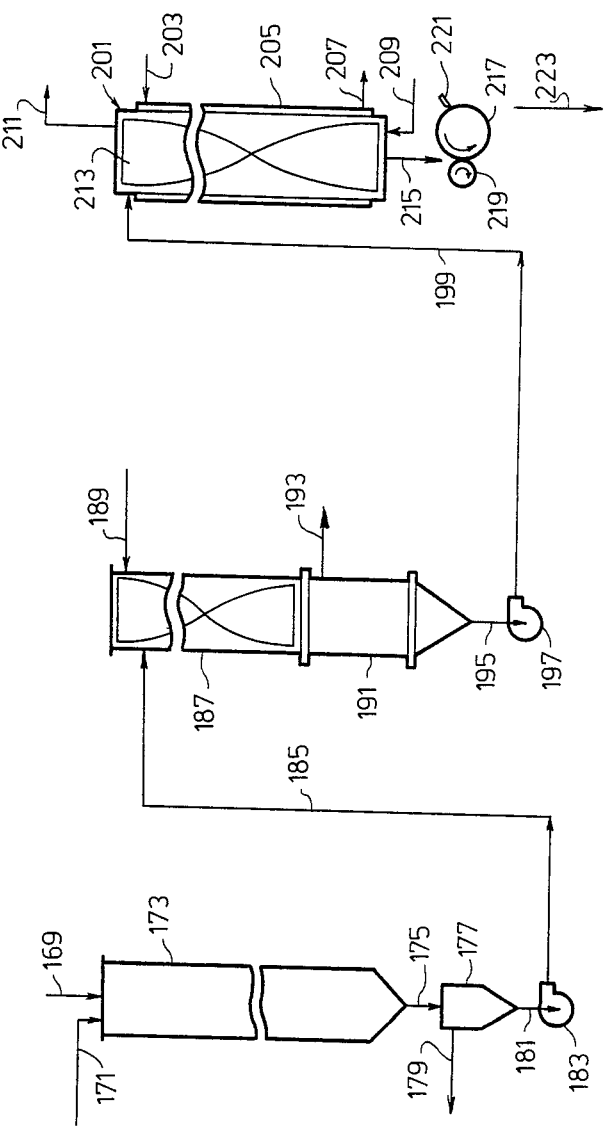

The invention will be readily understood by reference to the description thereof in this specification, taken in conjunction with the drawing in which:

FIG. 1 is a schematic representation of the apparatus of the invention, illustrating the feeding of detergent acid and neutralizing agent to a wiped film neutralizer, and the removal of desired high solids concentration detergent salt solution from such neutralizer; and FIG. 2 is another schematic representation, illustrating the making of neutralized detergent salt in solid form from starting organic material, sulf(on)ating agent and neutralizing agent.

In FIG. 1 film reactor 11 is charged with reactants through lines 13 and 15 and respective inlets in the reactor wall (not shown), the former line being for addition of lipophilic sulf(on)atable material and the latter being for charging of sulfonating agent, which is normally gaseous sulfur trioxide. The sulf(on)ating reaction takes place in the film reactor and the product of the reaction, which will include separable waste gases, is removed from the reactor through an outlet therein (not shown) and through discharge line 17, and is delivered to separator 19 wherein waste gases are removed through line 21. From the separator 19 the acid mix produced is taken off through line 23 and is delivered to a collector 25, from which it may be pumped via line 27 and metering pump 29 through line 31, rotameter 33 and valve 35, and either line 37, valve 39 and line 40 or line 41, valve 43 and line 44, into wiped film reactor 45. Temperature and pressure gauges 47 and 49, respectively, allow monitoring of the conditions of the feed and aid in calibrating the rotameter, if that is considered to be desirable.

A source of air under pressure (not shown) is communicated with line 51, pressure controlling valve 53, feed pot 55 (which contains neutralizing solution 57), line 59, heat exchanger 61, line 63, rotameter 65, line 67, pressure control valve 69 and line 71, which enters wiped film neutralizer 45 through an inlet opening therein (not specifically shown), which is at a location above inlets (not shown) which communicate with lines 39 and 43 for addition of the detergent acid. Coolant enters heat exchanger 61 through line 62 and exits via line 64. Pressure gauges 73 and 75 are provided, as well as temperature gauge 77, so that the pressure on the neutralizing agent in the feed pot can be determined, as can be the pressure and temperature of such agent prior to control valve 69 and prior to entrance of the neutralizing agent solution into the wiped film reactor to effect neutralization of the detergent acid. Pipings 79 and 81 communicate sight glass 83 with feed pot 55 so that the height of the neutralizing solution in the pot can be visually monitored. Make-up feed of neutralizing solution 57 is stored in make-up tank 85, which communicates through passage 87, metering pump 89 and line 91 with line 59 and feed pot 57 to recharge the feed pot or to maintain the height of neutralizing solution 57 relatively constant in such pot. Weighing means identified by numeral 93 are provided to measure the weight of the neutralizing solution in the make-up tank (and the amount thereof fed to neutralizer 45).

Wiped film reactor 45, which is vertically cylindrical in shape, and has an interior free space or volume 101, includes a plurality of wiping blades 95, preferably three or more, depending on the size of the reactor. Such blades or scrapers are mounted at a suitable angle, such as about 5°, on rotating shaft 97, which is coaxial with the cylindrical reactor 45, and which is driven by motor 99 (preferably a constant speed motor) in such a direction (clockwise when viewed from the top in the embodiment illustrated) that blades 95 help to move contents (not illustrated) of the neutralizer 45, with the aid of gravity, downwardly through the neutralizer (as well as outwardly onto wall 111) and into holding pot 103. Thus, even if some gelled material were to be produced due to a temporary excess of moisture such would soon be removed from the neutralizer by the impelling actions of the inclined blades. An alarm can be provided to indicate gel production and that would warn an operator that the reactants' feed ratio was off specification and should be changed. Because of the short throughput time such correction can be made before the production of an appreciable amount of gelled product. A temperature gauge 105 and a pH meter 107 are located at the bottom of reactor 45, with probes thereof (not numerically identified, but diagrammatically illustrated) in clearance space 109 between blades 95 and inner wall 111 of the reactor to allow determination of the temperature and pH (as is) of the neutralized product at the base of the wiped film reactor, from which it is being fed to holding pot 103.

A vacuum is drawn on holding pot 103, and through it also on reactor 45, by a vacuum pump or other source of vacuum, not illustrated, with which line 113 communicates. The vacuum causes gaseous material, including condensables, to be withdrawn from pot 103 through line 115, condenser 117, line 119, condensate receiver 121, line 123, vacuum control valve 125 and line 113 to the vacuum pump. Condensate 127 may be withdrawn from the condensate receiver 121 through line 129, valve 131 and line 133. A pressure gauge (or vacuum gauge) 135 permits checking the operation of the vacuum controller. Coolant enters condenser 117 through line 137 and exits through line 139.

At the bottom of holding pot 103 means for withdrawing high active ingredient content neutralized detergent salt solution is provided, which includes plunging mechanism 141 in cylinder 143, which mechanism communicates with hose pump 145, line 147, valve 149, line 151, static mixer 153 and line 155 to recycle the detergent salt solution 157 through the holding pot. A pH gauge 159 and a pressure (vacuum) gauge 161 are provided for monitoring such product characteristics and for checking the flow conditions of the recycle loop. Neutralized product is taken off from the holding pot through line 163, valve 165 and line 167.

In FIG. 2 feed lines 169 and 171 deliver sulf(on)atable organic material and sulfur trioxide gas, respectively, to film reactor 173, wherein they are reacted to produce a detergent acid or acid mix, which is dropped through line 175 to a separator 177. Waste gases are removed through line 179 and detergent acid passes through line 181 to pump 183, from which it is directly pumped through line 185 to wiped film reactor or neutralizer 187. In reactor 187 the detergent acid produced in film sulfonator 173 is neutralized with neutralizing agent solution, which is delivered to the reactor through line 189. The wiped film neutralizer is maintained under vacuum by communication with holding pot 191, on which a vacuum is drawn through line 193. Water vapor is removed through piping 193, thereby concentrating the neutralized detergent and cooling it, due to the heat of vaporization extracted during vaporization of the water. Such cooling is especially useful when the detergent salt being made is heat sensitive, tending to decompose or thicken objectionably when heated. The neutral detergent solution produced is dropped from the holding pot 191 through line 195 to pump 197, which pumps it through line 199 to jacketed wiped film evaporator 201. The evaporator is heated by passing steam through line 203 into jacket 205 and removing condensate from the jacket through line 207. Draft air enters the evaporator through line 209 and exits through line 211 with water vapor that has been removed from the neutralized detergent base solution. Good contact with the reactor wall of the detergent base solution in film form is maintained by the rapid rotation of wiper blades 213, in essentially the same way such good contact is maintained with the interior wall of the neutralizing reactor employed. The dried product, in fluid form, is removed from evaporator 201 through line 215, from which it is delivered to chill roll 217, on which a film is formed due to the action of spreading roll 219. The cooled high solids content detergent, in solid film or sheet form, is removed from roll 217 by knife 221 and falls, as a solid sheet or chips, flakes or ribbons, to a collector, not shown, as represented by arrow 223. Alternatively, the cooled detergent may be milled and converted to chip form of desired thickness.

The detergents made by the process of this invention may be either sulfates or sulfonates and will usually be referred to, in the generic sense, as sulf(on)ates. Such detergents will normally include a lipophilic moiety containing an alkyl group having 8 to 20 carbon atoms therein, preferably being linear alkyl. The invention is applicable to the production of a wide variety of such detergents, including higher fatty alkyl sulfates, higher fatty alkyl lower alkoxy ether sulfates, higher alkyl benzene sulfonates (but often they can't be dried further in the evaporator because they become gummy), paraffin sulfonates, olefin sulfonates, and monoglyceride sulfates, for example, but is not to be limited to these. Preferably, the invented process is applied to neutralizing higher fatty alkyl sulfuric acid, higher fatty alkyl lower alkoxy ether sulfuric acid or higher alkylbenzene sulfonic acid, or a mixture of two or more such materials, in which the alkyl is of 10 to 18 carbon atoms, the lower alkoxy is of 2 to 3 carbon atoms, and from 1 to 5 (and sometimes more) lower alkoxy groups will be present in the higher fatty alkyl lower alkoxy ether sulfuric acid. Of the three preferred acids to be neutralized by the present process the most preferred is the higher fatty alkyl sulfuric acid. The preferred higher alkyl for the three preferred types of sulf(on)ated detergent salts to be made by the invented process will be of 10 to 14 carbon atoms, more preferably 12 or 13, or about 12 or 13 carbon atoms. For the alkyl alkoxy ether sulfate the lower alkoxy is preferably ethoxy and 2 to 4 ethoxy groups are present per mole, more preferably 3 or about 3.

The sulf(on)ic acid to be neutralized may contain usual byproducts of a sulfonation or sulfation process. Such detergent acid mixes can contain free oil (unreacted organic material), sulfuric acid, sulfur trioxide, water, and any impurities in the free oil or the sulf(on)ating agent, or reaction products thereof. The sulf(on)ating agent employed to make the detergent acid (or surface active agent acid) may be sulfur trioxide, sulfuric acid or oleum, providing that when neutralization is to be effected the free sulfuric acid content of the detergent acid is not so high that the sodium sulfate content resulting from the neutralization makes the product unacceptable for processing or for its desired use. Preferably, sulfur trioxide will be employed because it leaves little, if any, sulfuric acid in the detergent acid. Although concentrations of detergent acid as low as 50% (even lower in some instances) can be satisfactorily neutralized by the invented process, normally such concentrations will be greater than 80%, preferably more than 90% and more preferably more than 95%. Frequently, concentrations of the detergent acid over 97.5% are feasible and are much preferred, for example, when lauryl sulfuric acid is being neutralized, and in some processes such concentration has approached 99% (98.5%).

Various neutralizing agents may be employed, including alkali metal hydroxides, alkali metal carbonates, alkali metal bicarbonates, ammonia, lower alkanolamines (especially triethanolamine), and mixtures of such neutralizing agents. Among the alkali metals sodium is much preferred over potassium but potassium hydroxide, carbonate and/or bicarbonate may also be used. Most preferable is sodium hydroxide, in aqueous solution. The other neutralizing agents are preferably also in aqueous solution, when employed. In some instances the neutralizing agent can include very finely divided suspended neutralizing agent, too. Generally, the impurities content of the sodium hydroxide solution will be minimized and normally it will contain less than 2% of sodium chloride (solids basis) and only trace amounts of other impurities. The aqueous neutralizing agent solution (or solution-suspension) may be of any suitable concentration but normally will be in the range of 20 to 35% by weight, preferably 23 to 33% and more preferably 25 to 30%, with the latter two ranges also being specific for the preferred aqueous sodium hydroxide solution. Note that the moisture content of the neutralizing solution should be such that the combined moisture contents of the detergent acid and neutralizing agent, plus that formed in the neutralization reaction, should not cause gel formation. In other words, the detergent salt content of the aqueous detergent should be above the highest gel region salt content.

A wiped film reactor, which in accordance with the present invention is employed as a neutralizer, is the apparatus in which the present neutralization process is effected. Such reactor, which is like that of FIG. 1, includes a walled reaction zone and a plurality of scraper blades in such zone, usually 2 to 6, e.g., 3 to 5. The reaction zone is vertically cylindrical in shape, although it can be horizontal or inclined, and the scraper blades, which rotate about an axis coaxial with the cylindrical zone, travel at high speed and in close proximity to the inner wall of such walled reaction zone, so as continuously to remove material from such wall and deposit it at other locations thereon with great force, thereby repeatedly renewing the thin film, preventing local overconcentrations of reactants and speeding the reaction. The scrapers limit film buildup in the reaction zone, which could result in localized overconcentrations and localized overheatings, when vacuum is not employed, which could lead to deterioration of the detergent. Also, the repeatedly regenerated thin film which moves downwardly through the reaction zone, is more readily cooled by evaporation of any volatile solvents and other materials present, which assists in removing the heat of neutralization from the reaction zone. The use of vacuum also helps to prevent any objectionable overheating of the reactants and neutralized product.

The reactants are preferably admitted to the reaction zone near the top thereof and more preferably below the tops of the wipers. The wipers will normally extend to within 2 to 15 cm. of the top of the reaction zone, preferably to within from 2 to 5 cm. thereof. The topmost inlet(s) for the reactant(s) will desirably enter such reaction zone by passing through the reactor walls at a height from 1 to 10 cm. below the tops of the wiper blades. The reactant inlets may be of reduced diameters, compared to inlet piping, so as to minimize the likelihood of any material inside the reactor being forced back into the inlet lines. Thus, orifices have been included in the inlet lines (or in the reactor wall), with diameters of their openings being in the range of 0.8 to 3 mm., preferably about 1.5 mm. However, the orifice sizes will be variable, depending on the reactor sizes and feed rates.

In effecting the neutralization in the wiped film reaction zone it will usually be preferable for the neutralizing agent, such as aqueous sodium hydroxide, to be added to the zone above the levels at which detergent acid, such as lauryl sulfuric acid, enters such zone. This prevents hydrolysis of the detergent salt by acid. It is also preferable for the detergent acid to be fed to such zone at a plurality of heights over the height thereof, with the first entry for such acid often being from 2 to 10 cm. below the entry port for the neutralizing agent, and with other entries for the detergent acid preferably being in the upper portion of the reactor or distributed over the length of the reactor. Normally, from 2 to 10 entries for the detergent acid may be employed, preferably 2 to 5. While the reactants are desirably brought into the reaction zone in the manner described above it is within the present invention to add the detergent acid nearer to the top than the neutralizing agent, to employ plural neutralizing agent entries and/or a single detergent acid entry and to make other variations in the process, so long as both the detergent acid and neutralizing agent are brought into film reaction contact within the wiped reaction zone. However, fatty alcohol sulfate of desired high quality cannot usually be made using such variations and therefore such changes in the neutralization apparatus and process will be avoided if they result in an unacceptable product.

The neutralization reaction zone in the wiped film reactor is cooled primarily to prevent deterioration of the detergent. Such cooling may be effected by means of a cooling jacket on the reactor or by the addition to the reaction zone of a volatile solvent, to extract heat from the zone during vaporization. However, it is highly preferred to employ vacuum, which is preferably transmitted to the reaction zone through the holding pot, although other means of applying vacuum to the reaction zone may also be utilized.

In the embodiment of the invention illustrated in FIG. 1 a plunger and hose pump combination is shown for removing product from the bottom of the holding pot. Additionally, a recirculation system is illustrated for recycling product through the pot. It is to be understood that other pumping mechanisms may be employed and the one illustrated is that which was incorporated into pilot plant equipment so that if any gel were to form during the neutralization it could be pumped out of the equipment. However, such is not a problem when the process is operated according to the present instructions, and conventional pumping mechanisms may be substituted. With respect to the recycling of detergent salt, this tends to homogenize the product, evening out any pH variations that might occur. If the system were to be computer controlled the recycle loop might be of lesser importance, although its presence would always be desirable. Normally the period in which neutral detergent solution remains in the holding pot will be from 1 to 10 minutes, preferably 3 to 7 minutes, e.g., about 5 minutes, before exiting therefrom, often for subsequent drying. The product exiting from the holding pot and/or recycle loop, will be in the form of a pumpable aqueous solution or slurry which will normally contain from 50 to 85% by weight of detergent salt solids, preferably 60 to 80% by weight thereof, and more preferably as in the case of the production of sodium lauryl sulfate solution, at least 65 or 70%, very often at least 73% thereof, e.g., about 75%, with the balance of the solution being mostly water.

For the various neutralization reactions of this invention suitable temperatures under the circumstances will be employed. Normally, such neutralization temperature, which is the temperature in the reaction zone and in the communicating holding zone (the holding pot), will be at least 40° C., usually 40° to 70° C., preferably 45° to 65° C., as for the neutralization of lauryl sulfuric acid. The throughput time through the reaction zone will be from 0.5 or 1 to 30 seconds, preferably being 1 to 10 seconds and more preferably being from 1 to 5 seconds, e.g., 2 seconds. The holding pot will usually hold the neutralized product for from 1 to 10 minutes, preferably 2 to 7 minutes, e.g., about 5 minutes. During the time spent in the holding vessel the newly made detergent salt solution will be mixed with 2 to 10 parts of previously neutralized product, preferably 3 to 8 parts, e.g., about 5 parts, and mixing will preferably be effected by continuous "recycling" circulation. The ratio of neutralizing agent to detergent acid for the neutralization reaction will be approximately stoichiometric, usually being within a molar ratio of 0.95 to 1.03, preferably 1.00 to 1.02. The vacuum drawn on the reaction zone will usually be such that the pressure in such zone is from 25 to 500 torr, preferably being 50 to 250 torr, e.g., about 150 torr, as for making sodium lauryl sulfate. However, it may be modified so as to yield the desired temperature in the reactor, and therefore the vacuum depends to some extent on the detergent acid being processed and the desired solids concentration.

The scraper blades or vanes of the wiped film reactor will pass from 0.0 or 0.2 to 5 mm. of the interior wall of the reactor, preferably within 0.2 to 2 or 3 mm. thereof, e.g., 0.8 mm. They will be rotating at 1,000 to 4,000 r.p.m., preferably 2,200 to 3,200 r.p.m., e.g., about 2,500 r.p.m., and the blade tip speed will be in the range of 5 to 25 meters per second, preferably 8 to 15 m./sec., e.g., about 10 m./sec. The rotational speeds may be changed from the ranges given and depend to some extent on the reactor size, especially the inside diameter thereof. Tip speeds will generally be in the ranges previously given, even when reactor size is changed. The scraper blades or vanes employed are usually of a width which is within 10 to 45% of the internal diameter of the reactor and the width:thickness ratio of the vanes will be in the range of 3:1 to 20:1. The vanes will normally be made of corrosion resistant, strong material, such as an alloy of iron and chromium and/or nickel, or other suitable alloy, e.g., 301 stainless steel, Hastelloy C-276 or Inconel 625, and the means for joining the blades to the rotor, such as rivets, will often also be of the mentioned alloys, as frequently will be the rotor, too. Preferably the blades will be welded to the rotor. Other materials of construction which will withstand the condition of use may also be employed, such as engineering plastics, fiberglass reinforced polyethers, polypropylene, Teflon coated parts, etc. Similarly, the walls of the reactor may be of such materials, other alloys or glass, e.g., a borosilicate glass, such as Corning QVF, when such are sufficiently strong and resistant to chemical change from the reactants and products. The mentioned glass is preferred. The vanes preferably will be helically positioned along the rotor but in some instances longitudinal positioning will be satisfactory. The helical position is such that the bases of the vanes make an angle in the range of 1° to 15°, preferably 2° to 15°, and more preferably 2° to 10°, with respect to a longitudinal line along the rotor shaft, and the helically positioned vanes are so located that they will help to move the reactants and products in the reactor downwardly toward the exit.

Highly preferred operating conditions for the wiped film neutralizing reactor, especially when the detergent acid is a higher alkyl sulfuric acid, e.g., lauryl sulfuric acid, and the neutralizing agent is an aqueous solution of alkali metal hydroxide, e.g., sodium hydroxide, will be concentrations of the detergent acid of more than 97.5%, which acid contains less than 1.0% of sulfur trioxide and less than 1.5% of fatty alcohol, e.g., lauryl alcohol, and the hydroxide will be at a suitable concentration between 20 and 35% by weight in water, so as to result in the desired end product. As charged, the hydroxide temperature is in the range of 30° to 50° C. and the detergent acid temperature is in the range of 20° to 40° C. The height of the reaction zone in the reactor will usually be from 0.5 to 1.5 m. and the diameter thereof will be from 5 to 10 cm., but can be more. The number of vanes on the scraper is 3 or 4 but 2 can also be used. The vanes are usually of a width of from 15 to 25% of the internal diameter of the reactor and they are disposed at an angle in the range of 2° to 15° with respect to the scraper axis. The width:thickness ratio of the vanes is normally within the range of 5:1 to 10:1, the tip speed is within the range of 8 to 15 m./sec., the rotational speed of the vanes is within the range of 2,200 to 3,200 r.p.m. (but is variable to control the tip speed), and the clearance between the scraper blade tips and the interior of the reactor is from 0.5 to 1 or 2 mm. The pressure in the reactor is from 50 to 250 torr and the throughput time in the reaction zone is from 1 to 5 seconds. The reaction product is passed from the reactor to a holding vessel, in which vapors and entrained gases are separated from the product, and the product exiting from such vessel or chamber, e.g., sodium lauryl sulfate, is removed at a temperature in the range of 45° to 65° C., with the effective ingredient content of the product being at least 65% and the water content being no more than 28%. Thus, when sodium lauryl sulfate is made from sodium hydroxide and lauryl sulfuric acid by the process of this invention it will contain at least 65 or 70% of such active ingredient, with no more than 25 or 28% of water, no more than 1.2% of lauryl alcohol, no more than 1.5% of sodium sulfate and a negligible proportion, usually no more than 0.2%, of sodium hydroxide. Additionally, the color of the solution will be no darker than 75 Klett. The various processing conditions and apparatus structual and operating descriptions depend on the material being processed and on the apparatus size and design so such conditions and descriptions may be different from those given here, when appropriate.

In more preferred operations, the product removed from the holding pot will be at a temperature in the range of 52° to 62° C., will contain at least 73% of detergent salt, such as sodium lauryl sulfate, no more than 25% of water, no more than 1.0% of free oil, no more than 1.0% of sodium sulfate, no more than 0.1% of sodium hydroxide, and no more than 0.2% of sodium chloride. However, one can make a product containing as little as 0.6% of free oil and 0.7% of sodium sulfate. The product will also be of a color no darker than 25 Klett, e.g., 5 to 20 Klett.

To produce neutralized detergent salt of highest quality it is desirable to utilize the present neutralizing reactor in conjunction with the process and apparatus for producing the detergent acid. This is so because it is often important for the detergent acid to be neutralized promptly after manufacture to avoid hydrolysis or other decomposition on storage before use, especially when, as is often the case, an escess of sulfonating agent, e.g., $SO_3$, was used in manufacturing the acid. When a slight excess of sulfur trioxide gas is used to make higher alkyl sulfuric acid and the acid is held at elevated temperature for more than about five minutes, darkening of the color of the acid occurs, indicating degradation thereof. When the molar ratio of sulfur trioxide to lauryl alcohol for the sulfation reaction is within the range of 1.02 to 1.07, storage at a temperature of 50° C. or higher can cause appreciable color darkening after more than five minutes. Therefore, in accordance with this aspect of the invention, the detergent acid will be made in a film reactor by reaction of sulfur trioxide on sulf(on)atable organic moieties, such as lauryl alcohol, with the molar ratio of sulfur trioxide to such organic compound being within the range of 1 to 1.02 to 1.07, and the detergent sulfuric acid made by such sulf(on)ation process will be charged to the wiped film reactor for neutralization within five minutes, preferably within 2 or 3 minutes after removal from the film reactor in which it is produced.

It is preferred that the detergent salt made by the present neutralization process be converted to solid form for convenience in shipping and use, and to promote product stability. Such is desirably accomplished by feeding the sodium lauryl sulfate product at the temperature at which it is removed from the wiped film reactor, and after separation of vapors and gases therefrom, to a wiped film evaporator equipped with a heated jacket, through which evaporator air is passed and at which the temperature of the sodium lauryl sulfate (neutralization product) is raised to its boiling point under the conditions within the evaporator, which is usually over 70° C., often over 90° C. and not usually more than 110° C. After drying in the evaporator the dried detergent salt, such as sodium lauryl sulfate, will be at least 92% active ingredient and will contain no more than 6% of water, 1.5% of free oil and 2% of sodium sulfate. The pH of a 1% solution of the detergent salt will normally be in the range of 8 to 12, preferably 9 to 11, when such salt is sodium lauryl sulfate. To assist in evaporating the water from the detergent salt solution charged to the wiped film evaporator and to avoid water vapor issuing from the product discharge, draft air will be passed upwardly through the evaporator, usually at atmospheric pressure, and the dried product of the evaporator will be converted to solid film form on a chill roll or other suitable apparatus or combination of apparatuses, from which it may be removed in solid chip, ribbon or sheet form, ready for use, such as for incorporation in a dental composition, e.g., a dentifrice, as the detergent component thereof.

The neutralized detergent product from the wiped film neutralizing reactor will be in the liquid state, will not be gelled, and will not contain appreciable quantities of objectionable gel. This is so because the detergent acid charged will be essentially anhydrous and the amount of moisture present in the neutralizing agent will be sufficiently low so that the neutralized detergent resulting will have a solids content above that which gels with water. An advantage of having the neutralizing agent injected into the reaction zone first is that when the detergent acid is first contacted with moisture (that in the aqueous solution of neutralizing agent) it is simultaneously reacted with the neutralizing agent, such as sodium hydroxide, to form the salt, which is less susceptible to hydrolysis or other decomposition reactions. Thus, the neutralized detergent salt remains liquid and comparatively stable, in the film reactor (and in the holding vessel which may be joined with the reactor), in which the reactants and product remain for only a short time, after which the detergent salt may be quickly cooled and converted to stable solid form.

In the above description reference has been made to the neutralization of lauryl sulfuric acid with aqueous sodium hydroxide and elsewhere in this specification it has been mentioned that non-gelling detergents may be made in a range of concentrations from 50 to 85%. It will be recognized that different detergent salts have different gelation ranges with water and therefore it is considered that this range, while generally applicable to those detergents of greatest interest, may be varied, sometimes being expanded and at other times being contracted accordingly. Nevertheless, the principle of operation is essentially the same. By use of this invention, by employing the wiped film reactor for neutralization of the detergent acid and by using detergent acid and neutralizing solution of sufficiently low water contents, production of gel is avoided at the temperatures of reaction because the detergent content of the product is above such content for the gel range. Thus, it is not necessary to employ co-solvents to avoid gelation, and the cost of solvent recovery is saved.

In the apparatus embodiment of the invention the wiped film neutralizing reactor is employed in conjunction with a film sulfonating reactor and such are connected so that the organic sulfuric or sulfonic acid or mixture thereof produced in the film sulf(on)ating reactor may be directly conducted to the neutralizing reactor so that the detergent acid may be neutralized within no more than five minutes after its production. Preferably, such conducting will be within three minutes and more preferably within one or two minutes, and the means provided will be a metering pump which will pump the detergent acid mix, in liquid form to the neutralizer. Preferably the apparatus will also include a wiped film evaporator, equipped with heating means and through which air will be passed, to further concentrate the neutralized detergent from the wiped film neutralizing reactor, so that an essentially anhydrous product, usually over 95% solids, and in molten form, may be produced. Such product is preferably fed to a chill roll, on which it is converted to solid film form, and from which it is removed by a cutting knife or other means, in sheet, ribbon, chip, flake or other suitable solid form. While it is most desirable for the sulf(on)ator, neutralizer, evaporator and solidifier (chill roll) to be employed together, other means of producing the detergent acid may be utilized and apparatus combinations of the wiped film neutralizer and evaporator, preferably with the solidifier too, are also within the invention. The materials of construction of the sulfonator and evaporator will usually be like those previously described as being suitable for the neutralizer.

The following examples illustrate but do not limit the invention. Unless otherwise indicated, all parts are by weight and all temperatures are in °C.

EXAMPLE 1

Utilizing a wiped film reactor like that illustrated in FIG. 1, equipped with a surge pot or holding pot below it, and equipped with recycling lines, hose pump and plunger, as illustrated in FIG. 1, lauryl sulfuric acid is neutralized with aqueous sodium hydroxide solution. The acid mix containing lauryl sulfuric acid (sometimes called sulfated lauryl alcohol) includes about 0.6% of sulfur trioxide, about 0.7% of free oil (lauryl alcohol) and about 98.7% of detergent acid (lauryl sulfuric acid). The color of the detergent acid is light enough so that the neutralized detergent salt made from it by neutralization with sodium hydroxide solution in the wiped film evaporator is usually in the range of 5 to 20 Klett for a 5% aqueous solution of the detergent salt.

The wiped film neutralizer employed includes a cylindrical borosilicate glass tube, the internal diameter of which is 7.6 cm. which contains a three-bladed rotor, coaxial with the cylinder. The cylinder is 78.2 cm. long and the rotor blades extend from 6 cm. from the top of the tube to 0.5 cm. from the bottom of the tube. The rotor blades are 0.16 cm. thick and 0.95 cm. wide and the shaft to which they are affixed by welding, rivets or other suitable fastening means, is 1.75 cm. in diameter. The blades, shaft and rivets are all made of No. 316 stainless steel, and the blades are equidistantly positioned along helices on the shaft that are inclined at 5° to longitudinal lines along the shaft. The clearance between the blade tips and the interior of the reactor is 0.7 mm. The aqueous sodium hydroxide solution is a 27.9% solution in water and when added to the reactor it is at a temperature of 37.8° C. The caustic inlet to the reactor is located so that its center point is 8.3 cm. from the top of the reactor tube, below the tops of the wiper blades, and in preferred embodiments of the invention the inlet is equipped with a circular orifice of a diameter of about 1.5 mm., to prevent any backflow of materials from the reactor into the supply line. The detergent acid enters the reactor through ports located so that their centers are 12 cm. and 23.6 cm. from the reactor top and they are equipped with orifices like that described for the inlet for the neutralizing solution. The lauryl sulfuric acid charged is at a temperature of 26° C. when it enters the neutralizer. Rotor speed is 2,500 r.p.m., which equals a tip speed of about 9.8 m./sec. The internal pressure in the neutralizer is 125 torr and at such pressure sufficient moisture and its heat of vaporization are removed from the reactor so that the temperature of the product exiting to the holding vessel is 57° C. The throughput time is about two seconds, on the average, and the holdup time in the holding vessel is about three minutes. The ratio of product:recycle in the holding pot is about 1:5. The hose pump employed is of the peristaltic type, with a replaceable nitrilo rubber (Buna N) hose section. The product removed from the neutralizer contains 75% of sodium lauryl sulfate, 0.6% of lauryl alcohol, 0.7% of sodium sulfate, 0.2% of sodium chloride, 0.1% of sodium hydroxide and 23.4% of water.

Sodium lauryl sulfate is made by the described process of this invention by reacting 88.4 parts of acid mix, containing 87.1 parts of lauryl sulfuric acid (molecular weight of the lauryl=179), 0.5 part of sulfur trioxide and 0.8 part of lauryl alcohol (commercial grade, a mixture of lauryl and myristyl alcohols), with 47.2 parts of aqueous sodium hydroxide containing 13.2 parts of sodium hydroxide, 0.2 part of sodium chloride and 33.8 parts of water, in the neutralizer previously described, under the mentioned reaction conditions. 125.3 Parts of neutralized sodium lauryl sulfate detergent solution are produced and 10.3 parts of vapors are removed from the holding vessel. During the neutralization reaction 5.8 parts of water are formed. The neutralized detergent contains 94 parts of sodium lauryl sulfate, 0.8 part of lauryl alcohol, 0.9 part of sodium sulfate, 0.2 part of sodium chloride, 0.1 part of sodium hydroxide and 29.3 parts of water.

The feed rates to the described reactor vessel for effecting the neutralization process of the invention are 12.2 kg./hr. of the sodium hydroxide solution and 23.2 kg./hr. of the acid mix (lauryl sulfuric acid). The product removal rate is 32.2 kg./hr. and the vapor removal rate, from the holding pot, is 3.2 kg./hr.

The product resulting has a good color, less than 25 Klett, usually being 5 to 20 Klett, and is useful as a detergent for incorporation in various cosmetic, health care and cleaning products. The product can be used directly, without extraction, purification or drying, but it is preferred to dry it, by a process that will be described in Example 3. The neutralized detergent solution is especially useful in dentifrices because of its good color and high purity, and when it is employed in substitution for commercially available sodium lauryl sulfate in a commercial dentifrice, it makes a superior product. Stability tests run on such a product show that it is storage stable. It maintains a substantially constant pH (about 10.5) after three weeks accelerated aging at 60° C., which is considered to be a severe test, and the constancy of the pH means that the product is stable. Similar aging tests show approximately constant lauryl alcohol concentrations, indicating that little or no degradation on normal storage is encountered.

In variations of the above procedures, different acid mix throughput rates and different concentrations of sodium hydroxide are utilized, so that different quantities of water vapor are removed in the neutralizer, yielding products of different moisture contents, so that the sodium lauryl sulfate content is in the range from 55 to 80% and the temperature is maintained in the range of 40° or 45° to 70° C. (or sometimes 80° C.). The temperature of the reaction depends on the vacuum employed and the amount of water removed during the neutralization depends on the heat of neutralization of the reactants and on reactants quantity. Below about 40° C. products of higher solids content in the 50 to 85% sodium lauryl sulfate range tend to solidify and above 80° C. degradation becomes a problem. Although the various detergent solutions made, at concentrations between 55 and 80%, are flowable at temperatures in the 50° to 60° C. range, it is found that at about 50 to 60% sodium lauryl sulfate content the apparent viscocity is at a peak, from which it drops to a low at 75 to 80%, e.g., 77% concentration, after which it rises again. However, with the equipment described the product is flowable over the mentioned broad range so that even if controls are not precisely effected variations in the moisture content of the product within the range given will not cause interruptions in the manufacturing process.

When the lauryl sulfuric acid employed is of a molecular weight of about 277 and when instead of lauryl sulfuric acid an alkyl sulfuric acid is charged which is of 14 or 16 carbon atoms, results similar to those reported for the lauryl sulfuric acid in the above example are obtainable. Similarly, when instead of sodium hydroxide, other neutralizing agents, such as potassium hydroxide, ammonia, triethanolamine and suitable akaline alkali metal salts or mixtures thereof, such as sodium hydroxide and triethanolamine, are employed as neutralizing agents, with manufacturing conditions being modified in accordance with the material(s) used, useful neutralizations are effectable. Satisfactory results are also obtainable when different wiped film reactors are utilized, with different numbers of blades, different blade designs, e.g., longitudinal positioning or variations in the angles at which the helices are mounted, different operating temperatures, rotor speeds, blade clearances, vacuums and feed rates. However, such should be as described in this specification.

EXAMPLE 2

In conjunction with the wiped film neutralizer of Example 1 there is employed a film reactor for manufacturing the lauryl sulfuric acid charged to the neutralizer. Such reactor, like those illustrated in FIGS. 1 and 2, is connected by piping and pumping means to the wiped film neutralizer, so that products from the reactor may quickly be delivered to the neutralizer, often in as little as two minutes, so as to avoid possible degradation before neutralization. The reactor, unlike the relatively short wiped film neutralizer, will preferably be of the long tube, Allied-type design, approximately 6.1 m. long and of 1.9 cm. internal diameter. The material of construction may be any material which does not adversely react with the contents of the reactor, such as a suitable alloy steel, e.g., stainless steel. Glass and suitable synthetic organic polymeric plastics, e.g., polypropylene, can be used but heat transfer through such materials is not good and therefore they are not preferred. Various types of alkanols or other organic detergent precursors may be employed, such as lauryl alcohols derived from petroleum or from natural coconut oil. For example, synthetic lauryl alcohol derived from petroleum and sold by Ethyl Corporation has been found to be satisfactory, as have been lauryl alcohols that were derived from coconut oil and natural products.

The ratio of sulfur trioxide to lauryl alcohol, on a molar basis, will normally be within the range of 1.00 to 1.07, preferably being 1.01 or 1.02 to 1.07 and more preferably being 1.01 or 1.02 to 1.04, e.g., about 1.02, which appears to be the best ratio. The lower the ratio, the more free oil is present in the product and the higher the ratio, the more sulfur trioxide is present. At the higher ratios, and also at higher temperatures, degradation of the detergent acid proceeds more rapidly and the color of the product is not as good. Additionally, taste may be adversely affected, which is important when the neutralized product is used in an oral preparation, such as a dentifrice.

62.7 Parts of lauryl alcohol and 25.7 parts of sulfur trioxide gas are charged to the film reactor, the gas being at room temperature and the lauryl alcohol being at about 30° C. Dwell time in the reactor is within 0.5 to 10 seconds, usually being within 1 to 5 seconds, e.g., 2 seconds. Waste gases are removed and the liquid product resulting, 88.4 parts of acid mix, contains 87.1 parts of lauryl sulfuric acid, 0.8 part of lauryl alcohol and 0.5 part of sulfur trioxide. Such material is then charged, within two minutes of removal from the sulf(on)ator, to the wiped film neutralizer previously mentioned, to produce the neutralized detergent salt described in Example 1.

Instead of employing lauryl alcohol (M.W.=197) various other aliphatic alcohols, such as myristyl alcohol and cetyl alcohol, may also be used, as may be lauryl alcohol of a molecular weight of 186, and essentially the same results are obtainable. In the present instance the sulfur trioxide employed is obtained by evaporation of liquid sulfur trioxide but catalytic sulfur trioxide, obtained by oxidation of sulfur dioxide, and diluted with air or nitrogen, may also be used.

EXAMPLE 3

A product from Example 1 (and/or Example 2) is dried in a wiped film evaporator operating at atmospheric pressure, to produce a dried product containing 94.0% of sodium lauryl sulfate, 0.8% of free oil, 0.9% of sodium sulfate, 0.2% of sodium chloride, 0.1% of sodium hydroxide and 4% of water. In variations of such experiment moisture content may be decreased to 3, 3.5, 4.5 and 5%. Of course, higher moisture contents are also possible, but are not usually desirable.

The wiped film evaporator employed is like that described with respect to FIG. 2 and is of materials of construction essentially like those of the wiped film neutralizer, except that a heat conductive material, such as an alloy steel, may be used for the evaporator wall. The feed of detergent salt solution is delivered to the evaporator by means of a Moyno pump, with the feed line from the pump to the evaporator being steam traced and insulated. The evaporator operates at atmospheric pressure, with draft air passing vertically upwardly through it. The jacket steam is under pressure (3.5 atmospheres, gauge) and the product exiting from the evaporator is molten and flowable, and is at a temperature of 105° C.

125.3 Parts of the neutralized detergent solutions from the wiped film neutralizer are fed to the wiped film evaporator and 25.3 parts of water are removed from the solutions in the evaporator. The rotor speed is 2,600 r.p.m., with the tip speed thereof being 9.8 m./sec. The dried molten product drops onto a chill roll, containing water at a temperature of about 20° C., to cool the product and then the production of the ribbons obtained is converted on a mill to chips 0.13 mm. thick, and about 1 cm. square. The production rate from the evaporator is about 20.5 kg./hr. of dried detergent.

The product made is at a temperature of about 25° C. or lower when it is removed from the chill roll. It is white in color, contains about 98% of sodium lauryl sulfate, on a dry basis, yields a pH in 1% aqueous solution of about 10 and desirably is of a moisture content of 3.5±0.5% (below 2.5% moisture the chips tend to become powdery). The chips are stable at room temperature, and at 37° C. and 80% relative humidity, over a period of six months, exhibiting no bacterial contamination. They are excellent components of high quality dentifrices and when incorporated in a commercial toothpaste formula at a concentration of 1.5%, as the only detergent component of the toothpaste, yield a light colored, good tasting, sweet smelling product.

EXAMPLE 4

Instead of employing lauryl sulfuric acid, as in Example 1, Sulframin 1298 acid mix (98% dodecyl sulfonic acid, 1% dodecyl benzene and 1% sulfuric acid) is neutralized by a process like that of Example 1. Equimolar proportions of the sulfonic acid and sodium hydroxide solution (of the composition of Example 1) are charged to the neutralizer, with the acid mix being at a temperature of about 34° C. and the sodium hydroxide solution being at a temperature of about 32° C. The rotor speed is 2,350 r.p.m. and the reactor pressure is about 240 torr. No recycle from and to the holding pot is employed and the product throughput rate is 51 kg./hr. The product made is at a pH of about 11.2 and the sodium dodecyl benzene sulfonate content thereof is 63.3%, with the balance being mostly water, except for small proportions of alkyl benzene, sodium sulfate and sodium chloride, as in the reactants. The product is flowable, satisfactorily light in color and useful as a detergent in cleansers and other compositions in which a high active ingredient content, high purity surface active agent of good color is a desirable component. Similar reactions can be run with other alkyl benzene sulfonic acids of 10 to 18 carbon atoms in the alkyls, e.g., tridecyl-, tetradecyl-, pentadecyl- and hexadecyl benzene sulfonic acids.

EXAMPLE 5

The procedure of Example 1 is repeated, as in Example 4, but with the sulfuric acid of lauryl polyethoxy ethanol (with three moles of ethylene oxide per mole) as the detergent acid. The sulfuric acid is made by reacting the ethoxylated alcohol (Neodol ® 25-3) with sulfur trioxide. A 74.5% solids content neutralized detergent is made from it by reacting the sodium hydroxide solution of Example 1 with the lauryl alcohol polyethoxy sulfuric acid. The detergent acid starting material contains about 97% of such acid, with the balance being about equally divided between free oil and sulfur trioxide (or sulfuric acid). The sodium hydroxide solution is at a temperature of about 25° C. and the acid mix is at 43° C. The rotational speed of the wipers is 2,400 r.p.m., the film reactor pressure is about 110 torr, and the dwell time is about two seconds. The product exits from the reactor at a temperature of 53° C. and is of an active ingredient content of about 70%. The color of the product is good (64 Klett for a 5% solution) and the pH, as is, is about 10. Such detergent is light colored and is satisfactory for use in cosmetics, health care products and detergent compositions.

In some instances, mixtures of the acid mixes of Examples, 1, 4 and 5 may be used, either two-component or three-component, sometimes with approximately equal amounts of each type being present. By practicing such processes, desired mixtures of neutralized detergent salts may be made, and may be concentrated and solidified, as described in Example 3.

The various advantages of the invention have been mentioned and have been illustrated in the working examples. To summarize, high quality detergent salts may be made by processes which directly produce high concentrations of such salts without undesirable byproducts. This is accomplished by neutralizing detergent acid with a neutralizing agent with only so much water present (usually almost all with the neutralizing agent) that the detergent salt solution made will be of a detergent salt content above the gel range for that product. Costly extraction operations are not needed to purify such products and concentration operations can be avoided. The apparatuses operate efficiently, with relatively low power consumptions, and effectively produce high quality products which can be employed as either high concentration liquids or solids. Such can be accomplished because of the excellent controlled reactions that are effectable in the wiped thin films created in these processes, which processes are effected very quickly and prevent undesirable overconcentrations and overheatings of the reactants and products, which could cause degradation thereof. The production of the high active ingredient content neutralized detergent salts is possible by the present methods despite the fact that gels are formed at concentrations between the normally available low concentrations of such detergents in aqueous media and the present high concentrations. In the present processes such gels are not formed. Yet, even if the control of feed ratio of acid and base is lost, so that high pH (13 or higher) or low pH (2 or lower) materials are present in the reactor, causing viscosity increases, or if the water content puts the detergent salt in the reactor in the gel range, the scraper blades quickly clear the reactor of thickened product or gel, allowing correction of the conditions without reactor shutdown. The peristaltic pump does not become blocked by gel and therefore vacuum on the system will not be lost while the pump is being cleaned after accidental gel production (as might occur during experimental runs). It is considered that the present processes are unobvious and that their success is so spectacular that it can revolutionize the manufacture of high quality, high active ingredient content neutralized detergent salts.

The present invention has been described with respect to various illustrations and embodiments thereof but is not to be limited to these because it is evident that one of skill in the art, with the present specification before him or her, will be able to utilize substitutes and equivalents without departing from the invention.

What is claimed is:

1. A process for neutralizing organic sulfuric or sulfonic acid(s) or a mixture thereof, suitable for use as a detergent in neutralized salt form, which comprises feeding a liquid solution or slurry of neutralizing agent(s) and at least one organic acid containing a single sulfuric acid or sulfonic acid moiety and a higher lipophilic alkyl group of 8 to 20 carbon atoms, to a wall of a cylindrical reaction zone, the ratio of said neutralizing agent to said acid being approximately stoichiometric and the amount of water in said neutralizing agent being sufficiently low so that the neutralized detergent will have a solids content above the gel region; forming a film of said organic acid and said neutralizing agent on a wall of such zone; contacting said film with means which continuously produce agitating and wall wiping actions in said reaction zone to react said neutralizing agent(s) and said organic acid(s) by continuously removing and redepositing material on said wall while limiting the film buildup in said zone as said contacting means move said film through said reaction zone, said means comprising a plurality of scraper blades attached to a rotating shaft; continuing said contacting as the material moves through said zone in from one to thirty seconds while maintaining the temperature in said zone at 40° C. to 70° C., and removing the neutralized product from said reaction zone in the form of a pumpable aqueous medium containing a solids concentration of neutralized organic sulfate or sulfonate which is in the range of 50% to 85% by weight.

2. A process according to claim 1 wherein the alkaline neutralizing agent is an aqueous solution of alkali metal or ammonium hydroxide or alkanolamine, the acid is from the group consisting of higher fatty alkyl sulfuric acid, higher fatty alkyl lower ethoxy ether sulfuric acid and higher alkyl benzene sulfonic acid, in which the alkyl is of 10 to 18 carbon atoms and from 1 to 5 ethoxy groups are present in the higher fatty alkyl ethoxy ether sulfuric acid.

3. A process according to claim 2 wherein the neutralizing agent is an aqueous solution of sodium hydroxide, the organic acid is a higher fatty alkyl sulfuric acid of 10 to 14 carbon atoms in the alkyl group, the neutralization reaction takes place at a temperature of at least 40° C., and the detergent salt product removed from the wiped film reactor contains from 60 to 80% by weight of sodium higher fatty alkyl sulfate.

4. A process according to claim 3 wherein the reactor is vertically positioned and, said scrapers pass within from 0.2 to 5 mm. of the interior of the reactor.

5. A process according to claim 4 wherein the aqueous solution of sodium hydroxide and the higher fatty alkyl sulfuric acid are charged to the reactor through openings in the cylindrical wall thereof under a pressure which is sufficiently high to prevent any material inside the reaction zone from being driven out of said zone through said charging openings, the scraper blades extend for substantially the height of the reactor, the tip speed of the scraper blades is in the range of 5 to 25 meters per second, with the blade tips being within 0.2 to 3 mm. of the interior wall of the reactor.

6. A process according to claim 5 wherein the number of scraper blades is from 3 to 5, the blades are in helical disposition in the reactor and rotate in such a direction as to direct flowable material downwardly through the reactor, at least some of the openings in the cylindrical wall of the pressure in said reactor are near the top thereof, and the reactor is from 25 to 500 torr.

7. A process according to claim 6 wherein the opening in the reactor wall for charging of sodium hydroxide solution is above a plurality of openings in such walls, at different heights, for charging higher alkyl sulfuric acid, and the scraper rotates at a tip speed within the range of 8 to 15 m./sec.

8. A process according to claim 7 wherein the aqueous solution of sodium hydroxide is at a concentration between 20 and 35% by weight in water and, as charged to the reactor, is at a temperature in the range of 30° to 50° C., the higher alkyl sulfuric acid is lauryl sulfuric acid containing more than 97.5% of lauryl sulfuric acid, less than 1.0% of sulfur trioxide and less than 1.5% of lauryl alcohol, and is charged to the reactor at a temperature in the range of 20° to 40° C., the scraper blades are disposed at an angle in the range of 2° to 15° C., with respect to the scraper shaft so as to direct material downwardly through the reactor, the rotational speed of the blades is within the range of 1,000 to 4,000 r.p.m., the clearance between the scraper vane tips and the interior of the reactor is from 0.5 to 1 mm., the throughput time through the reaction zone is from 1 to 10 seconds, the reaction product is passed from the reactor to a chamber wherein, vapors and entrained gases are separated from the product, and the sodium lauryl sulfate product is removed from such chamber at a temperature in the range of 45° to 65° C., with the product removed containing, by weight at least 65% of sodium lauryl sulfate and no more than 28% of ater, 1.2% of lauryl alcohol, 1.5% of sodium sulfate and 0.2% of sodium hydroxide, and being of a color no darker than 75 Klett.

9. A process according to claim 5 wherein the lauryl sulfuric acid charged to the wiped film reactor is made in a film reactor by the reaction of sulfur trioxide on lauryl alcohol, with the molar ratio of sulfur trioxide to lauryl alcohol being within the range of 1.00 to 1.07, and the lauryl sulfuric acid is charged to the wiped film reactor for neutralization within five minutes after removal from the film reactor in which it is produced.

10. A process according to claim 9 wherein the sodium lauryl sulfate product from the wiped film reactor, after separation of vapors and entrained gases therefrom, is dried in a wiped film evaporator having a heated jacket which operates at atmospheric pressure with draft air passing upwardly through the evaporator to produce dried sodium lauryl sulfate containing at least 92% by weight of sodium lauryl sulfate.

11. A process according to claim 10 wherein the dried sodium lauryl sulfate product exiting from the reactor is passed to a chill roll on which it is converted to solid film form and from which it is removed in solid chip, ribbon or sheet form.

12. A process according to claim 1 wherein the neutralized organic sulfuric or sulfonic acid or a mixture thereof is produced in the wiped film neutralizing reactor in liquid state at a concentration which, at the temperature at which it is removed from the reactor, is above gel zone concentrations of the neutralized organic sulfuric or sulfonic acid or mixture thereof in water.

13. A process according to claim 12 wherein the organic sulfuric or sulfonic acid or a mixture thereof is a higher fatty alkyl sulfuric acid in which the alkyl is of 10 to 18 carbon atoms.

14. A process according to claim 10 wherein the organic sulfuric or sulfonic acid or a mixture thereof is a higher fatty alkyl ethoxy ether sulfuric acid in which the alkyl is of 10 to 18 carbon atoms and from 1 to 5 ethoxy groups are present.

15. A process according to claim 12 wherein the organic sulfuric or sulfonic acid or a mixture thereof is a higher alkyl benzene sulfonic acid in which the alkyl is of 10 to 18 carbon atoms.

16. A combination apparatus for producing an organic sulfate or sulfonate or a mixture thereof, suitable for use as a detergent, in the form of a pumpable aqueous medium containing a solids concentration of neutralized organic sulfate or sulfonate which is above the gel region and is in the range of 50% to 80% by weight which comprises (1) a film sulf(on)ating reactor having an internal wall, means for directing an organic material containing a higher lipophilic alkyl group of 8 to 20 carbon atoms which is sulfatable and/or sulfonatable by sulfur trioxide gas, to produce a detergent acid, onto said internal wall so that it will flow along said wall in a moving film and means for conducting sulfur trioxide gas onto said film to react with the organic material to produce an organic sulfuric or sulfonic acid or a mixture thereof having a concentration of more than 90% by weight of said acid; (2) a wiped film neutralizing reactor having an internal wall, means for directing organic sulfuric and/or organic sulfonic acid in liquid state onto said wall of the wiped film reactor in the form of a film, means for conducting a liquid solution or slurry of neutralizing agent for the organic sulfuric acid and/or organic sulfonic acid onto said wall of the wiped film reactor in the form of a film, and means for agitating the material on said wall and for scraping said internal wall to react said organic acid and said neutralizing agent while moving said mixture in film form past said agitating and scraping means in the wiped film neutralizing reactor to form a pumpable aqueous medium containing a solids concentration of neutralized organic sulfate or sulfonate which is above the gel region and in the ranges of 50% to 85% by weight; and (3) means for directly conducting to said wiped film neutralizing reactor, within no more than five minutes, the organic sulfuric or sulfonic acid or a mixture thereof produced in the film sulf(on)ating reactor.

17. A combination apparatus according to claim 16 which comprises, in addition, a wiped film evaporator having an internal wall, means for heating the interior of such evaporator, means for agitating material and for scraping the internal wall, means for passing air through such evaporator and means for feeding organic sulfate and/or sulfonate detergent from the wiped film neutralizing reactor to the wiped film evaporator.

18. An apparatus according to claim 17 which comprises, in addition, a chill roll positioned to receive evaporated detergent salt product from the wiped film evaporator, to convert such product to solid film form, and means for converting said solid film to sheet, ribbon or chip form.

* * * * *